United States Patent [19]

Schlight

[11] Patent Number: 5,051,503
[45] Date of Patent: Sep. 24, 1991

[54] POLYGLYCOL DICARBOXYLIC ACID AMIDE LUBRICANT AND FUEL ADDITIVES

[75] Inventor: Raymond C. Schlight, Fishkill, N.Y.

[73] Assignee: Texaco Inc., White Plains, N.Y.

[21] Appl. No.: 516,377

[22] Filed: Apr. 30, 1990

[51] Int. Cl.[5] .................... C07D 413/12; C07D 14/06
[52] U.S. Cl. ............................... 540/454; 252/51.5 R
[58] Field of Search ........................................ 540/454

[56] References Cited

U.S. PATENT DOCUMENTS 4,946,835  8/1990  Hirsch et al. ...................... 540/454

Primary Examiner—Robert T. Bond
Attorney, Agent, or Firm—Robert A. Kulason; James J. O'Loughlin; Vincent A. Mallare

[57] ABSTRACT

A lubricant/fuel additive which is the reaction product of polyoxyalkylene dicarboxylic acids and hydrocarbyl-substituted mono- and bis-succinimides of polyamines.

17 Claims, No Drawings

POLYGLYCOL DICARBOXYLIC ACID AMIDE LUBRICANT AND FUEL ADDITIVES

BACKGROUND OF THE INVENTION

Internal combustion engines operate under a wide range of temperatures including low temperature stop-and-go service as well as high temperature conditions produced by continuous high speed driving. Stop-and-go driving, particularly during cold, damp weather conditions, leads to the formation of sludge in the crankcase and in the oil passages of a gasoline or a diesel engine and deposits in the piston and cylinder, seriously limiting the ability of the crankcase oil to effectively lubricate the engine. In addition, the sludge with its entrapped water tends to contribute to rust formation in the engine. These problems tend to be aggravated by the manufacturer's lubrication service recommendations which specify extended oil drain intervals. Also diesel engines operate at a high temperatures and compression and frequently uses high sulfur fuels, generating excessive deposits on the piston and ring areas. Oils must be formulated with suitable dispersants and detergents to resist or remove such deposits.

It is known to employ nitrogen containing dispersants and/or detergents in the formulation of crankcase lubricating oil compositions. Many of the known dispersant/detergent compounds are based on the reaction of an alkenylsuccinic acid or anhydride with an amine or polyamine to produce an alkenylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a product having a relatively high level of nitrogen in order to provide improved dispersancy in a crankcase lubricating oil composition.

With the introduction of four cylinder internal combustion engines which must operate at relatively higher engine speeds than conventional 6 and 8-cylinder engines in order to produce the required torque output, it has become increasingly difficult to provide a satisfactory dispersant lubricating oil composition. Thus, it is an object of this invention to provide a novel lubricating oil additive.

Another object is to provide a lubricating oil composition which can withstand the stresses imposed by modern internal combustion engines.

DISCLOSURE STATEMENT

U.S. Pat. Nos. 3,172,892 and 4,048,080 disclose alkenylsuccinimides formed from the reaction of an alkenylsuccinic anhydride and an alkylene polyamine and their use as dispersants in a lubricating oil composition.

U.S. Pat. No. 2,568,876 discloses reaction products prepared by reacting a monocarboxylic acid with a polyalkylene polyamine followed by a reaction of the intermediate product with an alkenyl succinic anhydride.

U.S. Pat. No. 3,216,936 discloses a process for preparing an aliphatic amine lubricant additive which involves reacting an alkylene amine, a polymer substituted succinic acid and an aliphatic monocarboxylic acid.

U.S. Pat. No. 3,131,150 discloses lubricating oil compositions containing dispersant-detergent mono-and di-alkylsuccinimides or bis(alkenylsuccinimides).

U.S. Pat. No. 4,338,205 discloses alkenyl succinimides and borated alkenyl succinimide dispersants for a lubricating oil with improved diesel disperancy in which the dispersant is treated with an oil-soluble strong acid.

U.S. Pat. No. 4,482,464 discloses reaction products prepared by reacting hydroxyalkane carboxylic acids with reaction products of a polyamine and a hydrocarbyl succinic anhydride.

SUMMARY OF THE INVENTION

The present invention provides reaction products of polyoxyalkylene dicarboxylic acids with hydrocarbon-substituted mono and bis-succinimide of polyamines of the invention, as represented by the following formula

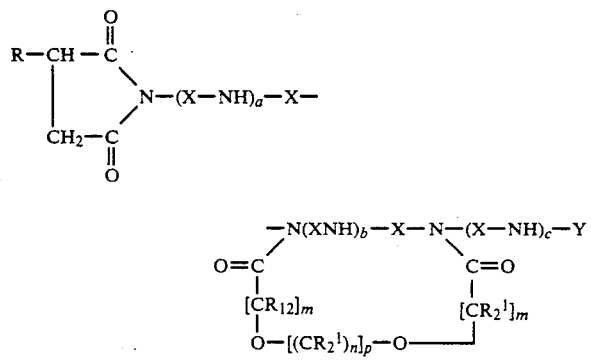

where R is a ($C_{25}$–$C_{500}$) hydrocarbyl radical; X is a ($C_2$–$C_6$) divalent alkylene radical; Y is H or a hydrocarbyl substituted succinimido alkyl radical having the formula:

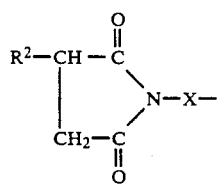

in which $R^2$ is a ($C_8$–$C_{500}$) hydrocarbyl radical; a is a number ranging from 0–4; b is a number ranging from 0–4; c is a number ranging from 0 to 4 and the sum of $a+b+c=0$ to 12. $R^1$ is H or a ($C_1$–$C_{20}$) alkyl group; m is a number ranging from 1 to 10 and n is a number ranging from 2 to 10; p is a number ranging from 1 to 50; or $R^1$ is a combination of one hydrogen atom and one alkyl group on at one or more of the "n" carbon atoms.

According to the present invention, alternative products could be formulated as two or more hydrocarbylsuccinimide molecules coupled by polyoxyalkylene diacid and molecules via formation of amide linkages.

DETAILED DESCRIPTION OF THE INVENTION

The present reaction products of polyoxyalkylene dicarboxylic acids with hydrocarbon-substituted mono and bis-succinimide of polyamines is represented by the following formula:

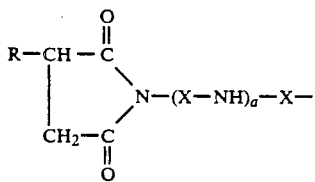

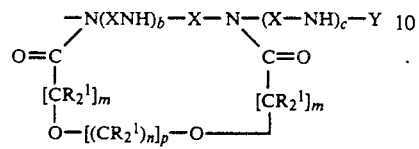

where R is a ($C_{25}$-$C_{500}$) hydrocarbyl radical; X is a ($C_2$-$C_6$) divalent alkylene radical; Y is ($C_2$-$C_4$) H or a hydrocarbyl substituted succinimido alkyl radical having the formula:

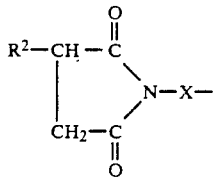

in which $R^2$ is a ($C_8$-$C_{500}$) hydrocarbyl radical; a is a number ranging from 0-4; b is a number ranging from 0-4; c is a number ranging from 0 to 4 and the sum of $a+b+c=0$ to 12. $R^1$ is H or a ($C_1$-$C_{20}$) alkyl group; m is a number ranging from 1 to 10 and n is a number ranging from 2 to 10; p is a number ranging from 1 to 50; or R' is a combination of one hydrogen atom and one alkyl group on at one or more of the "n" carbon atoms.

As shown and defined above, the present product additives are polyoxyalkylene (polyglycol) diacid amide derivates of a polyamine succinimide. Herein, they are referred to as polyglycol diacid amides.

Also, according to the present invention, the preferred compositions of the above formula (I) in the first instance (1) X=an ethylene radical; a=0; b=o; c=o; R is a ($C_{50}$-$C_{200}$) hydrocarbyl radical; Y is a succinimido ethyl group where $R^2$ is a ($C_8$-$C_{200}$) hydrocarbyl radical; $R^1$=H; m=1-3; n=2-4; and p=1-5; the second instance (2) wherein the values of X, a, b, r, m, n and p have the same values as in (1) above; c=0-2; and Y=H; or in the third instance, (3) wherein X, a, b, c; $R^1$; m; n and p have the same values as in (2) and Y is a mixture of H and $R^2$ [which has the same values as in (1)] in ratios of H: $R^2$=90:10-10:90.

The present invention is concerned with reaction products of diacid derivatives of poly (alkyleneglycols) with alkenylsuccinimides of polyalkyleneamines in order to prepare lubricant dispersants having improved dispersancy or fuel additives having improved dispersancy, carburetor cleanliness, rust and corrosion inhibition or other properties. These additives would also be expected to be improved over conventional alkenylsuccinimides in having minimal effects on the degradation of halogenated elastomers (e.g. Viton seals) owing to the reduction in the number of basic nitrogen functions in the dispersant by virtue of their reaction with the acid functions. Two types of products may be prepared by the subject derivatization process, either 1) macrocyclic diamides by reaction of the polyglycol diacid with two basic N atoms in the same alkenylsuccinimide molecule or 2) crosslinked products of two or more alkenylsuccinimide molecules with one or more polyglycol diacid molecules, or 3) mixtures of both types of products. The nature of each product would be determined by the number of basic amino groups in the alkenylsuccinimide intermediate and by the length of the polyglycol chain. Two or more basic N atoms (primary or secondary amino) per succinimide molecule are required to form a cyclic product; short chain polyglycol diacids (e.g. 1-10 ether links) are more likely to cyclize than longer chain diacids which are more likely to crosslink two or more succinimide molecules.

The present polyglycol diacids represented by the following general structure,

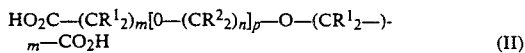

wherein m=1-10; n=2-10; p=1-50; $R^1$=H or a ($C_1$-$C_{20}$) alkyl, aryl or alkaryl group; and $R^2$=H or a ($C_1$-$C_{20}$) alkyl, aryl or alkaryl group.

In $(CR^1{}_2)_m$ or $(CR'_2)_n$ moieties, the R groups may be all the same or different R groups may be employed on either the same carbon atom or on other carbon atoms.

The preferred polyglycoldiacids are derived from polyethylene, polypropylene, polybutylene glycols or mixed polyglycols bearing ethylene, propylene and butylene moieties. The diacid derivatives may be prepared from polyglycols by such means as 1) oxidation of terminal primary alcohol functions, 2) reaction with halogenated alkanecarboxylic acids or their derivatives or 3) addition of the alcohol functions to unsaturated alkanecarboxylic acids or their derivatives.

The alkenylsuccinimides may be reaction products of ($C_{25}$-$C_{200}$) polybutenyl, polypropenyl, or other polyalkenylsuccinic acid anhydrides with polyalkyleneamines such as polyethylene amines, polypropyleneamines or polybutyleneamines. These imides may also be mono- or bis- imides or mixtures thereof.

An illustration of a polyglycol diacid prepared by nitric acid oxidation of tetraethylene glycol (see Example 1) has the following structure $$HO_2C-CH_2-(O-CH_2-CH_2)_2-O-CH_2CO_2H \qquad (IIA)$$

The reaction of this material, i.e., a polyglycoldiacid with a bis-alkenylsuccinimide of triethylenetriamine to form either a macrocyclic bis-amide (III) or a polymeric amide (IV) is shown below, where R=a 1300 average molecular weight polybutenyl group

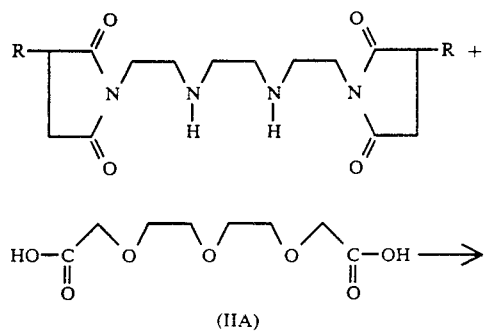

(IIA)

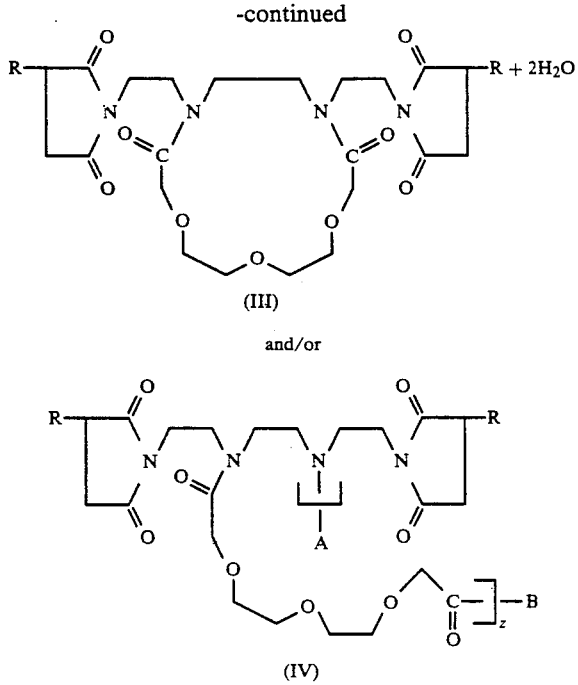

In structure (IV), z=degree of polymerization and the end groups of the polymer chain are satisfied wherein A is H or a carboxy-terminated polyether amide moiety and B is OH or a polyalkyleneamine succinimide moiety.

Structure (III) would be expected to be favored because the number of ring numbers, 15, falls in the range where ring formation is not hindered by bond strain (by analogy to the crown ether, 15-Crown-5).

The following examples illustrate the preparation of the diacid (IIA), and its reaction products with two different alkenylsuccinimides.

EXAMPLE 1

Preparation of Tetraethyleneglycol Diacid

Heated 198.0 g. (2.20 moles) of concentrated nitric acid (70%, wt) to 45C under a $N_2$-atmosphere and added 38.85 g (0.20 mole) tetraethylene glycol gradually via a dropping funnel at 45-55C, with cooling as needed. Then allowed the mixture to react for 1 hour at 50° C. before heating. Reacted further at 45° C. for 0.5 hour followed by 1 hour at 80° C. Cooled the solution to room temperature and then stripped at ~12 mm Hg pressure up to 70°-80° C. Continued stripping to constant weight (45.27 g yield vs. 44.45 g calculated for the diacid). The Neutralization No. was found to be 560 (vs. 505 calculated). The IR spectrum was as expected for the desired compound (Structure II).

EXAMPLE 2

Tetraethyleneglycoldiacid Amide of A Bis-polybutenylsuccinimide of Triethylenetetramine Combined 293.9 g (0.10 mole) of a polybutenylsuccinic anhydride (prepared from an ~1300 mol. wt. polybutene), 268.50 g paraffinic diluent oil, 125 ml. xylene and 7.31 g (0.050 mole) triethylenetetramine. Heated the mixture at reflux under $N_2$ for 3.25 hours at 146°-178° C., collecting ~2.0 ml. water until essentially water-free. Cooled the reaction mixture to less than 80° C. and then added 9.99 g (0.045 mole) of the tetraethyleneglycol diacid of Example 1. Then heated this mixture to reflux and reacted 5.5 hours at 178-181.5 until again essentially water-free, collecting 4.1 ml. water.

Finally, cooled to room temperature, filtered through diatomaceous earth and stripped off solvent at ~11 mm. Hg pressure to 120° C. The yield was 505.2 g fluid dark, product. The fluidity of the product indicates that the macrocyclic amide (III) had been formed as the major product rather than the polymer (IV). Satisfactory analyses were obtained, as follows:

| Test | Found | Calculated |
|---|---|---|
| % N | 0.53 | 0.53 |
| Total Acid No. | 2.4 | 0 |
| Total Base No. | 4.1 | 1.1 |

EXAMPLE 3

Tetraethyleneglycol-diacid Amide of a Mixed Mono/Bis-Polybutenylsuccinimide of Pentaethylenehexamine An ~50% oil concentrate of a 1:1 (molar) mixture of mono- and bis-polybutenylsuccinimides of pentaethylenehexamine was prepared from the same type of polybutenylsuccinic anhydride used in Example 2. Then 336.0 g (0.05 mole) of this concentrate was dissolved in 125 ml xylene and azeotropically distilled until water-free over 1 hour at 159°-164° C. This solution was cooled to 80° C. and 9.99 g (0.045 mole) of the diacid of Example 1 was added. This mixture was heated to reflux and 2.4 ml. water was collected over 9 hours at 175° C., max. Finally worked up the product as in Example 2, obtaining 322.6 g fluid product. Satisfactory analyses were obtained, as follows:

| Test | Found | Calculated |
|---|---|---|
| % N | 1.1 | 1.2 |
| Total Acid No. | 2.4 | 0 |
| Total Base No. | 16.8 | 22.0 |

The higher Total Base No. remaining in this product compared to Example 2 is due to the use of a higher ratio of basic amino groups in the intermediate imide: equivalents of diacid reactant (i.e. 4.5:1.8 vs. 2.0:1.8 in the case of example 2).

The dispersancy properties of the subject additives in a motor oil formulation were examined in the Bench VC test. This test evaluates the ability of an additive to disperse sludge and varnish precursors generated on heating nitrooxidized fuel components in the presence of the oil. The additives of examples 2 and 3 were compared to their parent alkenylsuccinimide, intermediates (2 int. and 3 int., respectively) in this test, with the results shown in the following table.

| | Bench VC Dispersancy Tests | | |
|---|---|---|---|
| | Test Results[1] at, % wt.[2] | | |
| Additive, Ex. | 4.0 | 5.0 | 6.0 |
| 2 | 42.0 | 20.0 | 12.0 |
| 2 int. | 49.0 | 41.5 | 32.0 |
| 3 | 13.0 | — | 8.0 |

-continued

Bench VC Dispersancy Tests

| Additive, Ex. | Test Results[1] at, % wt.[2] | | |
| --- | --- | --- | --- |
| | 4.0 | 5.0 | 6.0 |
| 3 int. | 25.0 | — | 12.0 |

[1]Low numbers (turbidity) reflect superior dispersancy; a number of about 10 or less is correlated with acceptable dispersancy in the API Seq. VC engine test.
[2]Blended into an SAE 30 grade motor oil formulation also containing Ca sulfonate and Ca alkylphenate detergents + zinc dialkyldithiophosphate antiwear agents + an ashless arylamine antioxidant + pour point depressant + an antifoamant.

The above test results show that in both cases (Example 2 and Example 3), the polyglycol diacid-treated imides were significantly better dispersants than the intermediate imides from which they were prepared. This indicates that the novel polyglycol diacid amide structures of this invention have a unique dispersancy effect. For example, the bis-succinimide intermediate of Example 2 is not very suitable as the sole dispersant in a gasoline engine lubricant but is rendered effective for that purpose on being converted to the polyglycoldiacid amide. Similarly, the mixed mono/bissuccinimide intermediate of Example 3, although effective as a gasoline engine oil dispersant, is rendered even more effective by the conversion to its polyglycol-diacid amide.

Also included in the present invention are products of the Example 2 and Example 3 types which are post-treated with other reactants such as carboxylic acids, hydroxy-substituted acids, urea, thiourea, isocyanates, isothiocyanates, boric acid or other boron reagents and alkylene oxides. Also alkenylsuccinimides may be pre-treated with such reagents prior to reaction with the polyglycoldiacids or variously substituted polyamines may be used to prepare the intermediate imides.

I claim:

1. A polyglycol diacid amide lubricant or fuel additive represented by the formula:

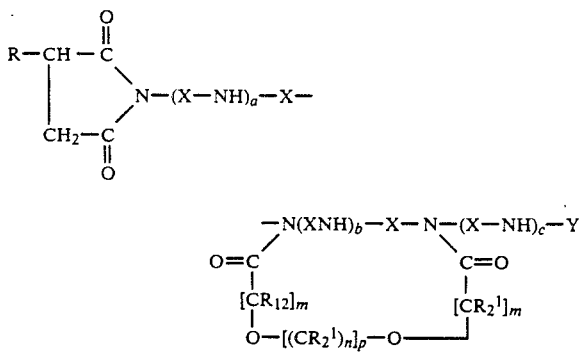

wherein R is a ($C_{25}$-$C_{500}$) hydrocarbyl radical; X is a ($C_2$-$C_6$) divalent alkylene radical; $R^1$ is H or a ($C_1$-$C_{20}$) allkyl radical; a=0-4; b=0-4; c=0-4 and a+b+c-=0-12; m=1-12; n=2-10; p=1-50;

Y is H or a hydrocarbyl substituted succinimido-alkyl radical having the formula

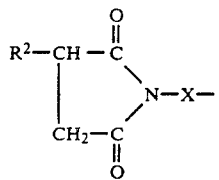

in which $R^2$ is a ($C_8$-$C_{500}$) hydrocarbyl radical; a is a number ranging from 0-4; b is a number ranging from 0-4; c is a number ranging from 0 to 4 and the sum of a+b+c=0 to 12; $R^1$ is H or a ($C_1$-$C_{20}$) alkyl group; m is a number ranging from 1 to 10 and n is a number ranging from 2 to 10; p is a number ranging from 1 to 50; or $R^1$ is a combination of one hydrogen atom and one alkyl group on at one or more of the "n" carbon atoms.

2. A method of preparing a polyglycol diacid amide lubricant/fuel additive represented by the following reaction equation

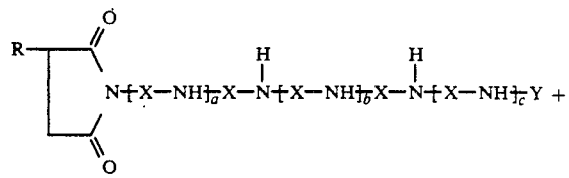

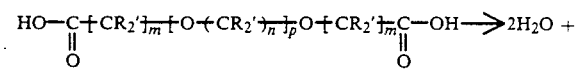

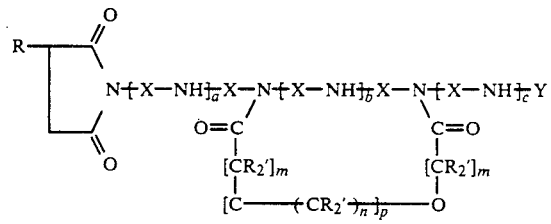

wherein $R^2$ is a ($C_{25}$-$C_{500}$) hydrocarbyl radical; X is a ($C_2$-$C_4$) divalent alkylene radical; R' is H or a ($C_1$-$C_{20}$) allkyl radical: a=0-4; b=0-4; c=0-4 and a+b+c-=0-12; m=1-12; n=2-10; p=1-50; Y is H or a hydrocarbyl substituted succinimido alkyl radical having the formula

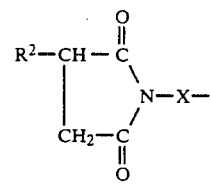

in which $R^2$ is a ($C_8$-$C_{500}$) hydrocarbyl radical; a is a number ranging from 0-4; b is a number ranging from 0-4; c is a number ranging from 0 to 4 and the sum of a+b+c=0 to 12; $R^1$ is H or a ($C_1$-$C_{20}$) alkyl group; m is a number ranging from 1 to 10 and n is a number ranging from 2 to 10; p is a number ranging from 1 to 50; or R' is a combination of one hydrogen atom and one alkyl group on at one or more of the "n" carbon atoms.

3. A method for preparing a polyglycol diacid amide lubricant/fuel additive as represented by the following reaction equation:

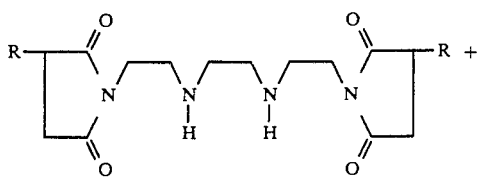

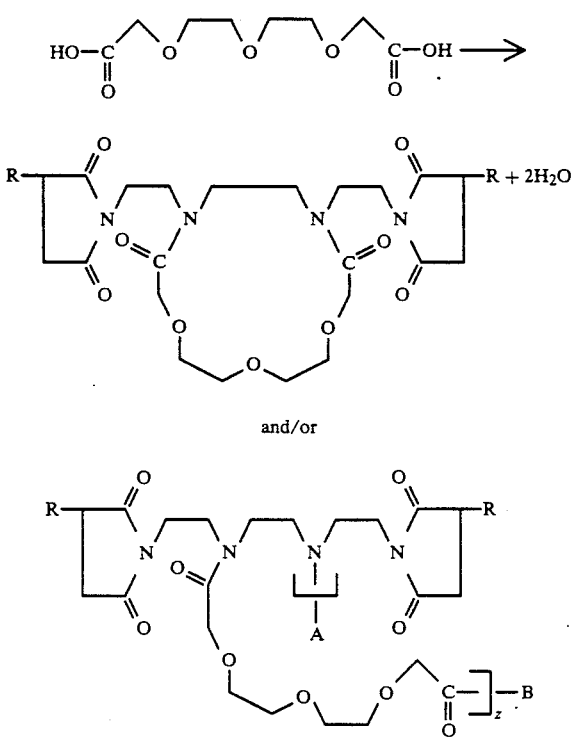

wherein R is a ($C_{25}$–$C_{500}$) hydrocarbyl radical A is H, or a carboxy-terminated polyether amide moiety; B is OH or a succinimide moiety; and z is the degree of polymerization.

4. The method of claim 1, wherein said polyglycol diacid is 3,6,9-trioxaundecane-1,11-dioic acid.

5. A method of preparing a polyglycol diacid amide comprises the steps of:
   a) reacting a hydrocarbyl substituted succinimide of a polyalkyleneamine with a polyglycol diacid at a temperature ranging from about 100° C. to about 200° C. at a pressure ranging from about 1 psi to about 100 psi, optionally, in the presence of an inert solvent or mineral oil diluent;
   b) continuing reacting said polyalkyleneamine at a temperature ranging from about 100° C. to about 200° C. for a sufficient time period to generate at least 80% of the reaction $H_2O$;
   c) separating the polyglycol diacid amide reaction product from the $H_2O$; and
   d) recovering the polyglycol diacid amide.

6. The method of claim 5 wherein said polyamine is a polyethyleneamine selected from the group consisting of a diethylenetriamine, diethylenetetramine, tetraethylene pentamine, pentaethylenehexamine; higher polyethylene amines and mixtures of polyethylene amines.

7. The method of claim 5 wherein said polyamine is bis-1,3-propylenetriamine.

8. The method of claim 5 wherein said polyamine is bis-1,6-hexylenetriamine.

9. The method of claim 5 wherein said polyamine is a branch-chained amine selected from the group consisting of N,N,N-tris-ethylamine, N,N,N-tris-propylamine and N,N,N-trisbutylamine.

10. The method of claim 5 wherein said polyamine is a mixed polyalkyleneamine selected from the group consisting of N,N-bis-aminopropyl-ethylene diamine, N,N'-bis-aminoethylpropylene diamine and N',N'''-bis-aminopropyl-diethylene-triamine.

11. The method of claim 5 wherein said polyglycol diacid is selected from the group consisting of: 3,6,9-trioxaundecane-1,11-dioic acid; 3,6,9,12-tetraoxatetradecane-1,14-dioic acid; and 3,6,9,12,15-pentaoxaheptadecane-1,4-dooic acid.

12. The polyglycol diacid lubricant/fuel additive of claim 1 wherein said R' is a ($C_{50}$–$C_{300}$) polybutenyl radical.

13. The polyglycol diacid lubricant/fuel additive of claim 1 wherein said R is a ($C_{80}$–$C_{200}$) polybutenyl radical.

14. The polyglycol diacid lubricant/fuel additive of claim 1 wherein said R is a ($C_{50}$–$C_{300}$) polypropylenyl radical.

15. The polyglycol diacid lubricant/fuel additive of claim 1 wherein said R is a ($C_{80}$–$C_{200}$) polypropylenyl radical.

16. The polyglycol diacid lubricant/fuel additive of claim 1 wherein said R is a ($C_{50}$–$C_{300}$) polybutenyl radical and $R^1$ is a ($C_8$–$C_{40}$) polybutenyl radical.

17. The polyglycol diacid lubricant/fuel additive of claim 1 wherein said R is a ($C_{50}$–$C_{500}$) hydrocarbyl radical, Y is H, and R is a ($C_{50}$–$C_{500}$) hydrocarbyl radical.

* * * * *